United States Patent [19]

Gupte et al.

[11] Patent Number: 5,575,280
[45] Date of Patent: Nov. 19, 1996

[54] POWDER INHALATION DEVICE HAVING NOZZLE TO EMPTY DOSING CHAMBER

[75] Inventors: Arun R. Gupte; Heinrich Kladders, both of Ingelheim; Hans D. Ruthemann, Gau-Algesheim; Bernd Zierenberg, Bingen, all of Germany; Raimo K. A. Auvinen, Kuopio, Finland; Pekka J. Karttunen, Varkaus, Finland; Mika T. Vidgren, Kuopio, Finland

[73] Assignees: Boehringer Ingelheim KG, Germany; Orion Corporation, Finland

[21] Appl. No.: 328,546

[22] Filed: Oct. 25, 1994

Related U.S. Application Data

[63] Continuation of Ser. No. 66,148, filed as PCT/EP91/02105, Nov. 7, 1991, abandoned.

[30] Foreign Application Priority Data

Nov. 29, 1990 [GB] United Kingdom ............... 9026025

[51] Int. Cl.[6] ............... A61M 15/08; A61M 16/00; B05D 7/14; B65D 83/06
[52] U.S. Cl. ............... 128/203.15; 128/203.23
[58] Field of Search ............... 128/203.12–203.15, 128/203.21, 203.19, 203.23, 203.24; 604/58

[56] References Cited

U.S. PATENT DOCUMENTS

| 2,587,215 | 2/1952 | Priestly | 128/203.15 |
| 3,973,566 | 8/1976 | Mathes | 128/203.15 |
| 4,274,403 | 6/1981 | Struve | 128/203.15 |
| 4,307,734 | 12/1981 | Blankenship | 128/203.15 |
| 4,570,630 | 2/1986 | Elliott et al. | 128/203.15 |
| 4,668,218 | 5/1987 | Virtanen | 604/58 |
| 4,709,837 | 12/1987 | Erdman | 222/636 |

FOREIGN PATENT DOCUMENTS

| 625927 | 5/1991 | Australia . | |
| 0079478 | 5/1983 | European Pat. Off. | 128/203.15 |
| 3535561 | 5/1986 | Germany | 128/203.15 |
| 097858 | 4/1977 | Taiwan | 128/203.15 |
| 162537 | 7/1991 | Taiwan | 128/203.15 |
| 2165159 | 4/1986 | United Kingdom | 128/203.15 |
| WO82/01470 | 5/1982 | WIPO . | |

Primary Examiner—Kimberly L. Asher
Attorney, Agent, or Firm—Sterne, Kessler, Goldstein & Fox P.L.L.C.

[57] ABSTRACT

The invention relates to a propellant-free inhalation device with a supply of pulverized medical substance in a supply chamber, which has a rotatable dosing means with one or more dosing chambers to receive in one defined position the dose of the medical substance to be inhaled from the supply chamber and to discharge the dose in another position. The inhalation device further is provided with a mouthpiece for active inhalation and an air channel to distribute the dose discharged from the dosing chamber in the flow of breathing air.

18 Claims, 3 Drawing Sheets

POWDER INHALATION DEVICE HAVING NOZZLE TO EMPTY DOSING CHAMBER

This application is a continuation of application Ser. No. 08/066,148, filed as PCT/EP91/02105, Nov. 7, 1991, now abandoned.

BACKGROUND OF THE INVENTION

1. Field of the Invention

This invention relates to an inhalation device.

2. Related Art

A propellant-free inhalation device with a supply of pulverized medical substance in a supply chamber, a manually actuatable metered dosing means in form of a rotatable dosing means having one or more peripheral recesses (dosing chambers) to receive in one position from the supply chamber the dose of the medical substance to be inhaled and to discharge the dose in another position, with a mouthpiece, formed at the side of the housing of the inhalation device for active inhalation and with an air channel for distributing the discharged dose in the breathing air flow and with at least one air intake embodied within the housing is described in DE 35 35 561.

In the known inhalation device the mouthpiece is arranged in such away that its axis extends parallel to the axis of the dosing means. Its air channel is guided underneath the dosing means to the opposite side of the housing where the air intakes are situated, by forming a cavity on the level of the dosing chamber. If due to a rotation of the dosing means the loaded recess (dosing chamber) is facing the air channel of the mouthpiece, the dose of powder that has been before discharged from the supply chamber falls, due to the gravity forces and—if desired—supported by a vibrating mechanism from the dosing chamber into the cavity of the air channel and is therefrom inhaled into the lungs of the patient by means of active inhalation. The air channel has a throttle area which is destined to promote the mixing of air with the medical substance by means of turbulence.

The known inhalation device has two critical drawbacks. On one hand the accuracy in dosing the powder to be inhaled and in emptying the dosing chambers is not satisfactory, on the other hand a reliable dispersion of the powder in the breathing air is not warranted. For proper handling of the known device both hands are necessary. Emptying of the dosing chamber and getting all the powder out of the mouthpiece is not guaranteed.

SUMMARY OF THE INVENTION

It is the object of the present invention to construct an inhalation device, starting from the above mentioned propellant-free inhalation device, in which the inhaled dose is reproducible at a high level of accuracy and in which a complete dispersion of the medical substance into the breathing air is achievable.

This object is achieved according to the invention by the following features: The main axis of the mouthpiece and the axis of the dosing means form an angle in the range of 70° to 110°, preferably 90°. The air channel is led on the level of the dosing means directly to the periphery of the dosing means, offset from the outlet of the supply chamber. The air intake is formed at the attachment area of the mouthpiece and is extended to the periphery of the dosing means in the orifice area of the air channel.

In the propellant-free inhalation device of the invention the air intakes are therefore arranged in such a way, respectively the paths of the air ducts are chosen such, that immediately at the beginning of the inhalation process air is led directly into the filled dosing chamber of the dosing means and that the same is intensively flushed by the inflowing air. The sucked-in air therefore blows the dosing chamber clean. Because of the relatively short air path between dosing chamber and the orifice of the mouthpiece the blown-out dose is received by the patient nearly completely. The actually inhaled dose therefore is reproducible at a high level or accuracy in the propellant-free inhalation device of the invention; also a complete dispersion of the medical substance in the air stream is achieved.

In a feature of the embodiment the dosing means is received in a fixed hollow cylindrical body which has recesses corresponding to the width of the dosing chambers and being spaced apart on the circumference of the dosing means according to the angular distance of the dosing chambers, said recesses being located on one side in the area of the supply chamber and on the other side in the area where the air channel of the mouthpiece and the air intake discharge into the cylindrical body.

Such an embodiment creates a clear separation, free of retroactions, between the receipt of the dose to be inhaled from the supply chamber on the one hand and the discharge of the dose to be inhaled into the air channel of the mouthpiece on the other hand.

Preferably, between the recess associated with the mouthpiece and a wall portion of the air channel of the mouthpiece, there is provided an opening for the passage of the intaken air directly at the periphery of the dosing means. An especially intensive air jet for cleaning off the dosing chamber positioned in front of the gap results when the gap is moulded like a nozzle.

Therapeutical preparations for inhalation often consist of a micronized drug and a less finely divided auxiliary substance which together form agglomerates (DE-A-1792207). Agglomerates are, however, also formed if the preparation only consists of uniformly micronized particles. Only the individual particles of the drug shall reach the deeper areas of the patient's lung. Therefore already in the mouthpiece of the device a separation of auxiliary substance and drug particles and desagglomeration (dispersion) should take place. For this purpose as high shear forces as possible should act on the agglomerates thus helping to disperse the particles adhering to each other. So according to another feature of the embodiment the cross-sectional shape of the air channel in the mouthpiece is adapted to create high shear forces.

This can be achieved, for example, if the air channel in the mouthpiece has a substantially constant cross-sectional area.

BRIEF DESCRIPTION OF THE DRAWINGS

Other features and advantages of the invention will become apparent from the description of the examples shown in the drawings.

DESCRIPTION OF THE PREFERRED EMBODIMENTS

Figure 1:
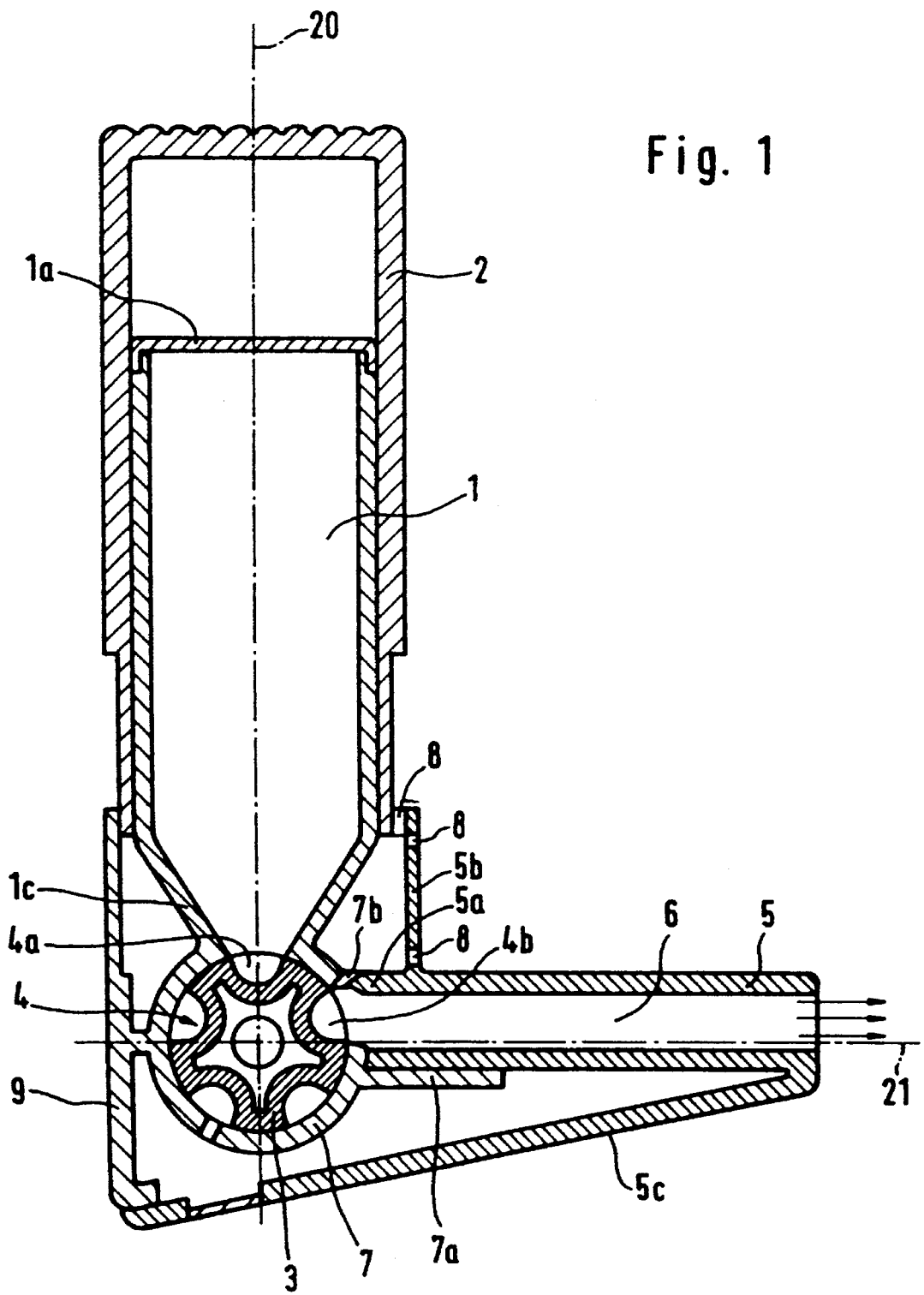
FIG. 1 is a longitudinal section through one embodiment of the inhalation device according to the present invention.

FIG. 1 shows a propellant-free inhalation device with a supply chamber 1 into which a certain supply of a pulverized medical substance to be inhaled is filled. As a rule, the amount is measured that it is sufficient for up to 300 single doses.

The supply chamber has a square cross-section (FIG. 2) and a lid 1a is tapered towards the bottom. A long extending cover 2 is put onto the supply chamber 1.

At the end of the conical portion 1c of the supply chamber there is a manually actuatable dosing means 3 in the form of a rotatable metering drum having five peripheral recesses 4, called dosing chambers. In the position of the dosing means shown in FIG. 1, the upper dosing chamber 4a is just being filled with the dose of medical substance to be inhaled from the supply chamber 1, while the earlier filled dosing chamber 4b is ready to be discharged.

At one side of the inhalation device a mouthpiece 5 is formed, through which the medical substance can be inhaled actively and which has an air channel 6 for distribution of the dose discharged from the dosing chamber 4b into the flow of breathing air. In the example illustrated, the main axis 21 of the mouthpiece 5 forms an angle of approximately 90° with the axis of the dosing means 3. The embodiment of the invention, however in no way is restricted to this form. Angles of approx. 70° to 110° can likewise be formed. The longitudinal axis of the mentioned air channel in the example is therefore perpendicular to the longitudinal (rotation) axis of the dosing means. In the vicinity of the dosing means the air channel is led at the level of the dosing means directly to its periphery. According to the position shown in FIG. 1 the air channel is thus directly opposite the dosing means, here the dosing chamber 4b.

The dosing means is received in a fixed hollow cylindrical body 7 which has recesses corresponding to the width of the dosing chamber 4, set off on the circumference by the angular distance of the dosing chambers 4a and 4b, the recesses being located on the one side in the area of the conical section 1c of the supply chamber and on the other side in the area where the air channel 6 of the mouthpiece 5 discharges.

In the area where the mouthpiece is attached, air intakes 8 are provided. The intaken air is led to an opening 7b between the recess of the hollow cylindrical body that is facing the mouthpiece and a partition wall 5a of the mouthpiece. From the opening the air arrives directly like a jet in the dosing chamber 4b and blows the powder contained therein out into the air channel 6 of the mouthpiece 5, without leaving any residue. It is preferred to mould the mentioned air supply opening 7b like a nozzle to create a strongly aligned stream of air.

Figure 2:
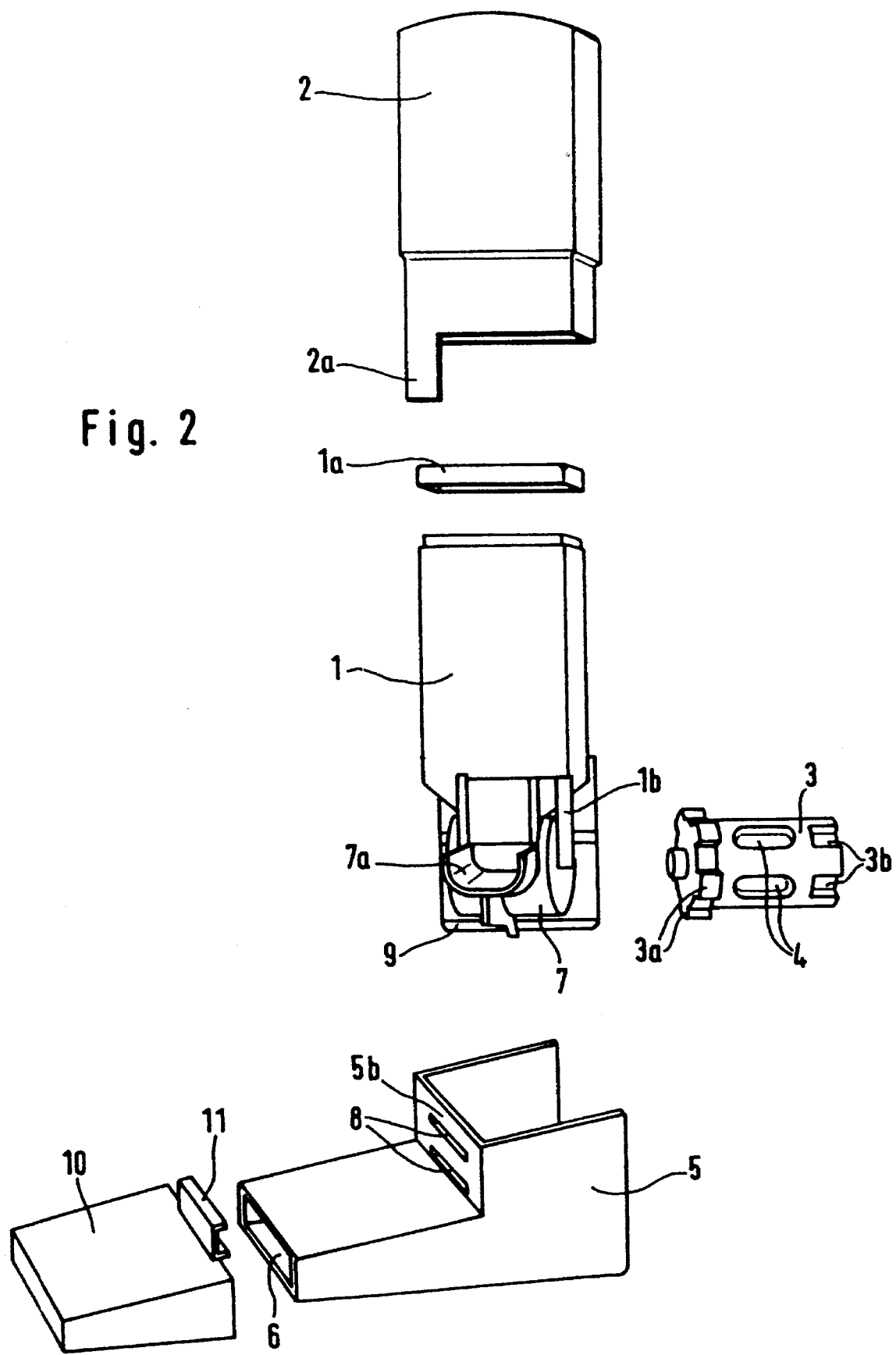
FIG. 2 is an explosive view of the structure of the inhalation device according to FIG. 1 in connection with other variants of parts of the device.

In FIG. 2 the structure of the inhalation device according to FIG. 1 is made clear in an explosive view.

The cover 2, together with the flap 2a, the function of which will be explained further below, is adapted to cover the supply chamber 1 and its lid 1a. Said lid closes the upper edge of the supply chamber.

An integral connection is provided between the supply chamber 1 and the hollow cylindrical body 7, which is adapted to mount the dosing means 3 with the dosing chambers 4. Moulded together with the supply chamber is also the rear wall 9 of the device, likewise the attachment 7a to receive the mouthpiece 5 including the wall 5b with the air intakes 8 and the air channel 6 as well as the bottom side 5c of the device (FIG. 1).

In addition to the dosing chambers 4, the dosing means 3 also has teeth 3a which are engaged with the flap 2a such that rotation can only be accomplished stepwise corresponding to the peripheral-distance between the dosing chambers 4 and the recesses in the body 7 (FIG. 1). The detent drive of the dosing means automatically aligns the dosing chambers with the outlet of the supply chamber on the one side and the air channel of the mouthpiece on the other side. Thus a good charging and discharging of the dosing chamber is ensured. Furthermore, the supply chamber 1 has a detent nose 1b which engages into recesses or notches 3b in the dosing means such that analogue to a ratchet rotation is only possible in one direction. It is thus possible to actuate the device just as the usual metered dose inhalers containing propellants.

To reduce friction between the dosing means 3 and the cylindrical body 7 different shapes and sizes of the slot 7c can be formed.

The mouthpiece can be closed with a cover 10 which comprises detent hoses 11 to engage into the air intakes 8 and subsequently close the same and take care of a safe sealing of the device. Furthermore, an unintended operation is prevented.

In another embodiment the cover 10 is connected to the mouthpiece or to the device so that it can be pulled off the mouthpiece, but cannot be completely removed from the device.

In another form of embodiment according to FIG. 1 the lid 1a of the supply chamber 1 for the medical substance may comprise a chamber, which, for example, is filled with silicagel or another drying agent to protect the medical substance against humidity.

Furthermore a vibrating mechanism can be provided, by means of which the medical substance is shaked when the device is operated, so that the respective dosing chamber receives a uniform charge. This vibrating mechanism, for example, can be formed by a ratchet in a manner known per se. The supply chamber 1 or the cover 2 can also have notches, which cause vibrations when these parts are moved relatively to each other.

Also for the design of the drive of the dosing means the man skilled in the art avails of several possibilities. In the simplest case this design can be embodied corresponding to the dosing devices in aerosol systems. Preferrably the drive is adapted to be rotated manually by means of a knob.

Also with respect to the detent drive and the "ratchet" other embodiments are imaginable.

The inhalation device desirably includes an arrangement, which prevents multiple doses to be discharged from the device.

The opening at the conical portion 1c of the supply chamber 1 is shaped for low friction forces of the dosing means in its bearing and easy rotation of the barrel without jamming.

For visual monitoring of the supply level in the supply chamber the supply chamber preferably is manufactured of usual transparent or translucent material. In the cover 2 a longitudinal slot or window may be provided, if desired with markings on it. These markings reveal the supply level, respectively the number of doses left.

The propellant free inhalation device according to the invention can also be provided with a dose counting system, where the counting steps can be derived from the rotation of the dosing means, for example via a gear system provided with numbers or by colour stripes.

Figure 3:
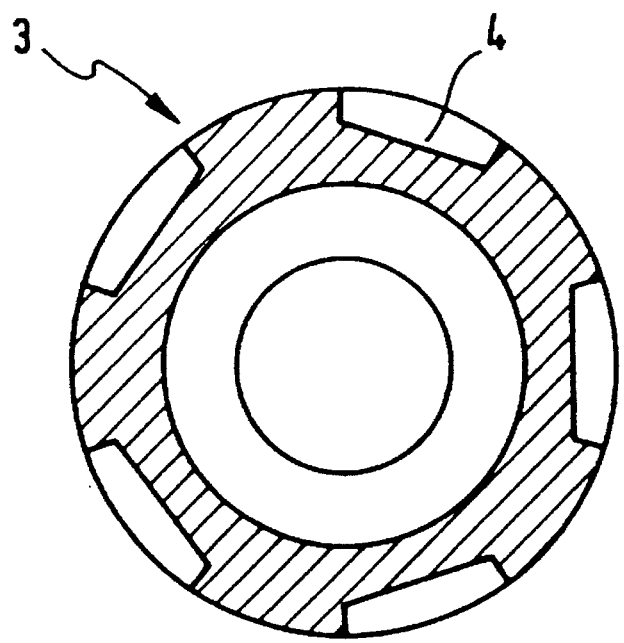
FIG. 3 is a cross section of a modified dosing means of the inhalation device.
Figure 4:
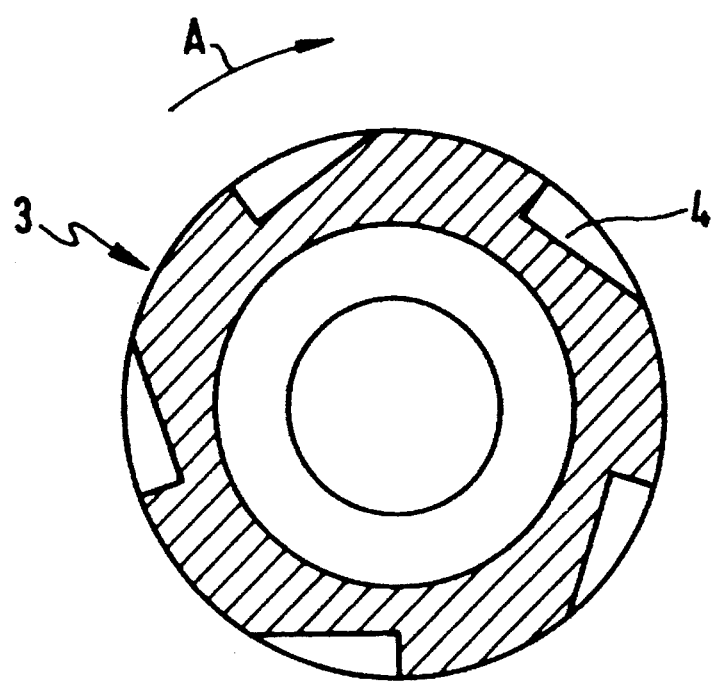
FIG. 4 is a cross section of another modified dosing means.

In the FIGS. 3 and 4 cross-sectional views of modified dosing means 3 are shown. In FIG. 3 the dosing chambers 4 of the dosing means 3 are flattened in the bottom area and embodied less deep compared to those of the previously described embodiment.

The dosing chambers 4 of the dosing means 3 in FIG. 4 show a triangular cross-section which are moulded in relation to the direction of rotation indicated by arrow A.

Moreover the axis 21 of the mouthpiece 5 not necessarily has to stand perpendicularly on the axis of the supply chamber 1 as illustrated in FIG. 1. Good results also have been obtained when the angle between the axes 20 and 21 generally lies in the range of 90° to 130°.

We claim:

1. A propellant-free inhalation device for use with a supply of pulverized medical substance, comprising:

a housing defining a supply chamber adapted to receive a supply of medical substance, said supply chamber having a longitudinal axis and an outlet;

manually actuatable dosing means for metering a dose of medical substance, said dosing means including a metering drum rotatable about an axis of rotation and having at least one peripheral recess which forms a dosing chamber for receiving a dose of medical substance from said supply chamber in a first position and for discharging a dose of medical substance in a second position;

a mouthpiece having a longitudinal axis connected to said housing for inhalation of a dose of medical substance, said mouthpiece including an air channel for distributing a dose of medical substance metered by said dosing means into an air flow drawn through said mouthpiece, said air channel positioned at the level of said dosing means and offset from said outlet of said supply chamber, wherein said longitudinal axis of said mouthpiece and said axis of rotation of said dosing means form a first angle in the range of 70° to 110°; and intaking making and channeling means for intaking and channeling air, said intaking and channeling means comprising at least one air intake and an opening positioned adjacent said dosing chamber in said second position, said opening forming a nozzle means for creating a strongly aligned stream of air and for emptying said dosing chamber, said nozzle means positioned at a periphery of said dosing means and in front of said dosing chamber, so that air that enters said air intake is channeled through said nozzle means to directly impinge on said dosing chamber in said second position to discharge a dose of medical substance from said dosing chamber directly into an air flow drawn into said air channel upon inhalation.

2. Inhalation device according to claim 1, wherein the cross-sectional area of said air channel in said mouthpiece is substantially constant.

3. Inhalation device according to claim 1, wherein said supply chamber is closed with a lid having on its inner side a chamber to take up a drying agent.

4. Inhalation device according to claim 1, further comprising:

a cover fitted over said supply chamber.

5. Inhalation device according to claim 4, wherein notches are provided on said cover of said supply chamber and that by a motion relative to a wall of said supply chamber vibrations are created.

6. Inhalation device according to claim 4, further comprising:

means for visual monitoring of the supply level in said supply chamber.

7. Inhalation device according to claim 6, wherein said supply chamber is manufactured from translucent material and said cover for said supply chamber has a longitudinal slot.

8. Inhalation device according to claim 1, further comprising:

a manually actuatable vibrating mechanism for vibrating a supply of pulverized medical substance.

9. Inhalation device according to claim 1, further comprising:

a plurality of dosing chambers; and means for rotating said dosing means which includes a stepping mechanism for stepwise rotation of said dosing means with a step length corresponding to the peripheral distance of said dosing chambers.

10. Inhalation device according to claim 1, further comprising:

means for counting the number of doses removed from said supply chamber.

11. Inhalation device according to claim 1, wherein said longitudinal axis of said mouthpiece and said longitudinal axis of said supply chamber form a second angle in the range between 90° to 130°.

12. An inhalation device according to claim 1, wherein said first angle is substantially equal to 90°.

13. An inhalation device according to claim 1, further comprising:

a fixed hollow cylindrical body for receiving said dosing means, said body defining first and second recesses each having a width defined by the angular distance of said dosing chamber along a circumference, said first recess positioned at said outlet of said supply chamber, and said second recess positioned where said air channel of said mouthpiece and said intaking and channeling means discharge into said cylindrical body.

14. An inhalation device according to claim 13, wherein said first angle is substantially equal to 90°.

15. Inhalation device according to claim 13, wherein said means for intaking and channeling air comprises an air passage formed between said second recess and a wall portion of said mouthpiece.

16. Inhalation device according to claim 15, wherein said air passage is molded to form a nozzle.

17. Inhalation device according to claim 13, further comprising:

a cover for said mouthpiece having detent elements to fit into said intaking and channeling means.

18. An inhalation device according to claim 13, wherein said longitudinal axis of said mouthpiece and said longitudinal axis of said supply chamber form a second angle in the range between 90° to 130°.

\* \* \* \* \*